United States Patent [19]

Djuric et al.

[11] Patent Number: 5,051,438
[45] Date of Patent: Sep. 24, 1991

[54] ALKOXY-SUBSTITUTED DIHYDROBENZOPYRAN-2-CARBOXYLIC ACIDS AND DERIVATIVES THEREOF, COMPOSITIONS AND USE

[75] Inventors: Stevan W. Djuric, Glenview; Thomas D. Penning, Elmhurst, both of Ill.

[73] Assignee: G. D. Searle & Co., Chicago, Ill.

[21] Appl. No.: 524,765

[22] Filed: May 16, 1990

[51] Int. Cl.$^5$ .................. A61K 31/415; A61K 31/42; C07D 405/12; C07D 413/12
[52] U.S. Cl. .................... 514/378; 514/406; 514/826; 514/863; 514/886; 514/887; 514/903; 548/247; 548/374
[58] Field of Search ............... 548/247, 374; 514/378, 514/406

[56] References Cited

U.S. PATENT DOCUMENTS 3,879,417  4/1975  Domergue et al. .............. 548/374
4,889,871  12/1989  Djuric et al. .................. 514/456

Primary Examiner—Robert W. Ramsuer
Attorney, Agent, or Firm—Roger A. Williams; Mary Jo Kanady; Paul D. Matukaitis

[57] ABSTRACT

This invention relates to compounds of Formula I and the stereoisomers and pharmaceutically acceptable salts thereof

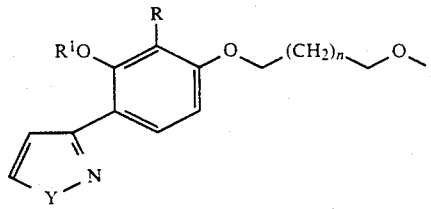

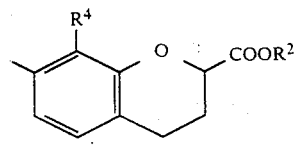

wherein
R is alkyl, alkenyl, alkynyl, or cycloalkylalkyl and m is 1 or 2;
$R^1$ is alkyl of 1 to 4 carbon atoms;
$R^2$ is hydrogen or alkyl of 1 to 5 carbon atoms;
$R^4$ is alkyl of 1 to 6 carbon atoms;
n is an integer from 1 to 5; and
Y is NH or oxygen.

The compounds of Formula I are leukotriene $B_4$ antagonists and are useful as anti-inflammatory agents and in the treatment of $LTB_4$ mediated diseases.

23 Claims, No Drawings

ALKOXY-SUBSTITUTED DIHYDROBENZOPYRAN-2-CARBOXYLIC ACIDS AND DERIVATIVES THEREOF, COMPOSITIONS AND USE

BACKGROUND OF THE INVENTION

1. Field Of The Invention

This invention is in the field of pharmaceutical agents which selectively act as leukotriene $B_4$ ($LTB_4$) antagonists and are useful as anti-inflammatory agents and for treating leukotriene $B_4$ mediated diseases.

2. Prior Art

Leukotriene $D_4$ and $C_4$ ($LTD_4/LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil stimulation and is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases.

*Gastroenterology*, 1985: 88: 580–7 discusses the role of arachidonic acid metabolites in inflammatory bowel disease.

*British Medical Bulletin*, (1983), vol. 39, No. 3, pp. 249–254, generally discusses the pharmacology and pathophysiology of leukotriene $B_4$.

*Biochemical and Biophysical Research Communications*, Vol. 138, No. 2 (1986), pp. 540–546 discusses the pharmacology of a specific $LTB_4$ antagonist which has a different structure than compounds of this invention.

U.S. Pat. No. 4,889,871 discloses alkoxy-substituted dihydrobenzopyran-2-carboxylate derivatives which are selective antagonists of $LTB_4$ with little or no antagonism of $LTD_4$ and are useful as antiinflammatory agents for treating inflammatory bowel disease. The compounds differ structurally from the compounds of this invention.

BRIEF DESCRIPTION OF THE INVENTION

This invention encompasses compounds of Formula I and the stereoisomers and pharmaceutically acceptable salts thereof:

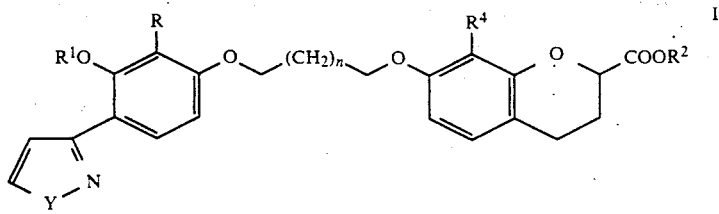

wherein
R represents alkyl having 2 to 6 carbon atoms, alkenyl having 2 to 6 carbon atoms, alkynyl having 2 to 6 carbon atoms, or $-(CH_2)_m-R^3$ wherein $R^3$ represents cycloalkyl of 3 to 5 carbons atoms and m is 1 or 2;
$R^1$ represents alkyl having 1 to 4 carbon atoms;
$R^2$ represents hydrogen or alkyl having 1 to 5 carbon atoms;
$R^4$ represents alkyl having 1 to 6 carbon atoms;
n is an integer from 1 to 5; and
Y represents NH or oxygen.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, psoriasis, asthma, and multiple sclerosis and in treating diseases mediated by $LTB_4$.

DETAILED DESCRIPTION OF THE INVENTION

This invention encompasses the compounds of formula I as previously described.

Preferred embodiments of the present invention are compounds of the formula II, the stereoisomers and pharmaceutically acceptable salts thereof,

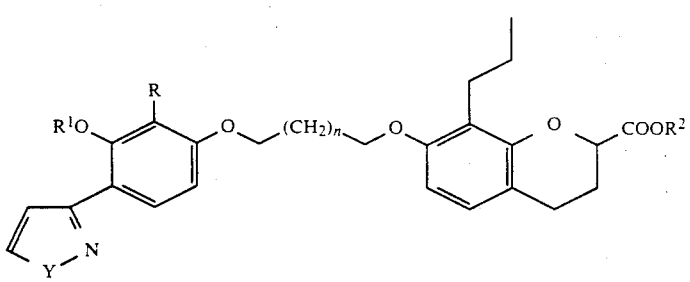

wherein
R represents alkyl having 2 to 4 carbon atoms alkenyl having 3 to 4 carbon atoms, or cyclopropylalkyl wherein the alkyl moiety has 1 to 2 carbon atoms;
$R^1$ represents methyl or ethyl;
$R^2$ represents hydrogen or alkyl having 1 to 3 carbon atoms;
n is an integer from 1 to 3; and
Y represents NH or oxygen.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, and psoriasis.

More preferred embodiments are compounds of the formula III and the stereoisomers and pharmaceutically acceptable salts thereof

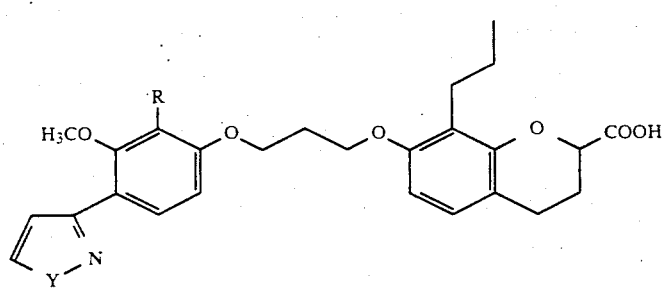

III wherein R represents propyl, 2-propenyl, or cyclopropylmethyl; and Y represents NH or oxygen.

Alkyl defined for R, $R^1$, $R^2$, and $R^3$ is straight or branched chain alkyl having the indicated number of carbon atoms.

Pharmaceutically acceptable salts such as ammonium, sodium, potassium, alkaline earth, tetraalkylammonium and the like are encompassed by the invention.

Scheme A shows a general method for preparing compounds of the invention.

As shown in Scheme A, the 4-acetyl compound (IV) is reacted with a formamide equivalent such as dimethylformamide dimethyl acetal to give the 4-[3-(dimethylamino)-1-oxo compound (V) which is then reacted with hydroxylamine hydrochloride to give the 4-(3-isoxazolyl) compound (VI). Hydrolysis of VI with an appropriate base such as lithium hydroxide gives the acid VII. Alternately V may be hydrolized with an appropriate base such as lithium hydroxide to give the acid VIII, then VIII can be reacted with hydrazine hydrate to give compound IX. Compound IX may be alkylated by reacting it with an alkyl halide or trifluoromethylsufonate to give the alkyl ester. ester. Pharmaceutically acceptable salts may be prepared from the acids by reacting them with an appropriate base.

SCHEME A

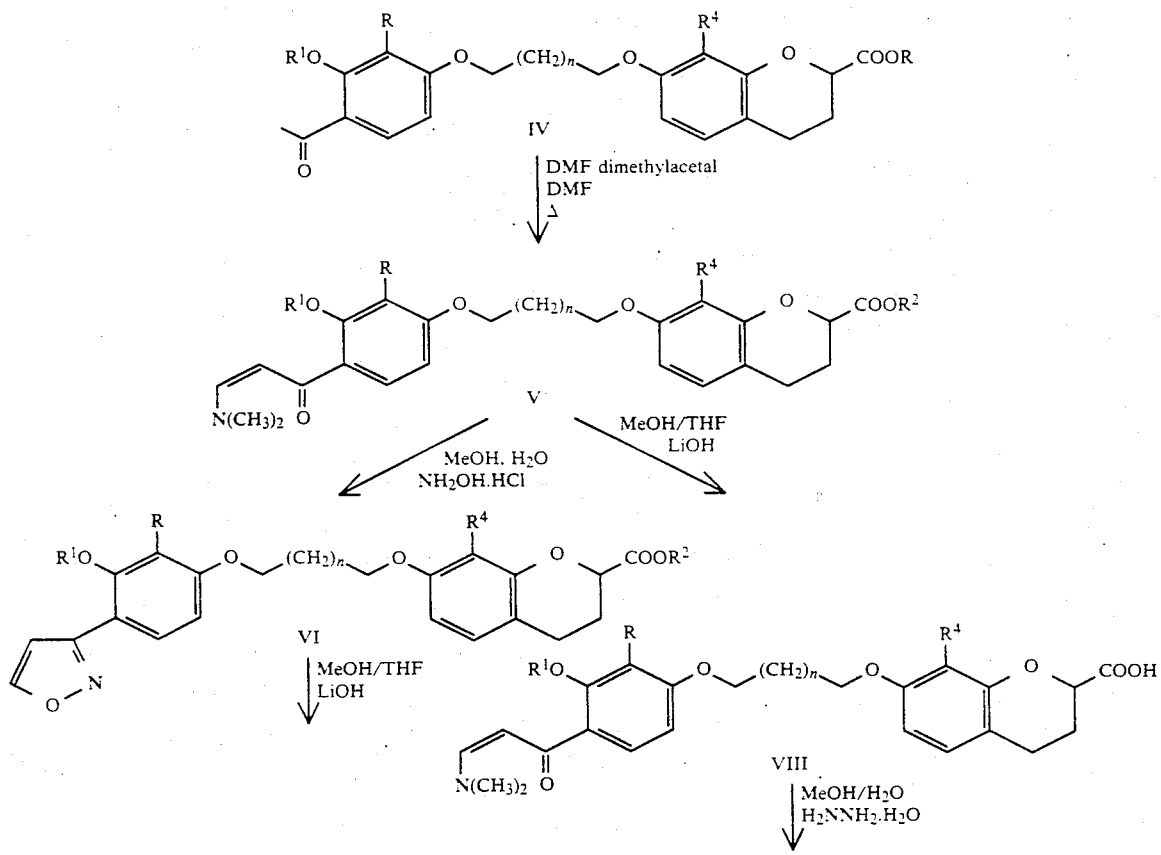

-continued
SCHEME A

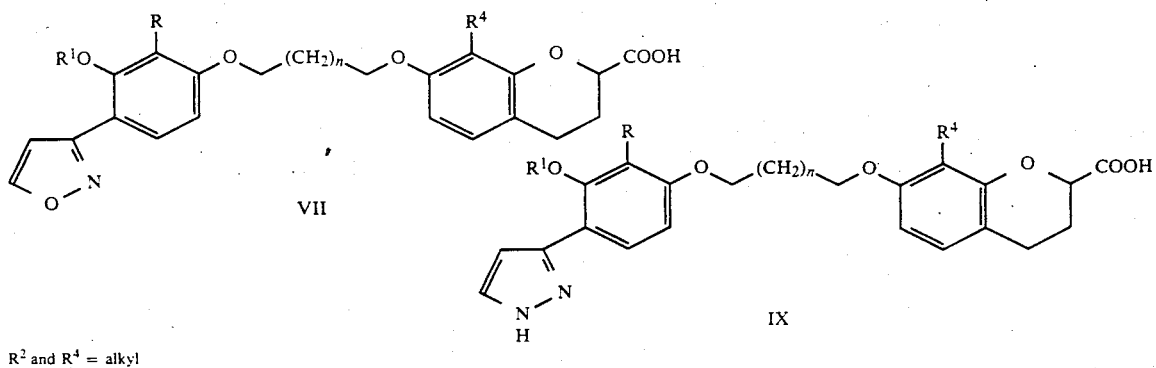

$R^2$ and $R^4$ = alkyl
R and $R^1$ are defined as hereinbefore

The biological activity of compounds of this invention is indicated by the following tests.

Preparation of Human Neutrophils

Neutrophils were purified from venous blood of normal human donors using standard techniques of dextran sedimentation, centrifugation on Ficoll-paque ® (Pharmacia) or Histopaque ® sterile solution (Sigma) and hypotonic lysis of erythrocytes (Boyum, A., *Isolation of Leukocytes From Human Blood: Further Observations. Scand. J. Lab. Clin. Invest.*, 21 (Suppl. 97): 31, 1968). The purity of isolated neutrophils was >95%.

LTB$_4$ Receptor Binding Assay

Neutrophils ($4-6 \times 10^6$) in 1 ml Hanks' balanced salt solution (HBSS) containing 10 mM HEPES buffer, pH 7.4 and 30 µM nordihydroguaiaretic acid were incubated with $0.6 \times 10^{-9}$M ($^3$H) LTB$_4$ in the presence or absence of test compounds. The incubation was carried out at 0° C. for 45 minutes and terminated by adding 5 ml of ice-cold HBSS followed by rapid filtration of incubation mixture under vacuum through GF/C glass fiber filters. The filters were further washed with 10 ml HBSS and radioactivity was determined. Specific binding was defined as the difference between total binding and nonspecific binding which was not displaced by $10^{-7}$M unlabeled LTB$_4$. All data refer to specific binding.

Modified Boyden Chamber Chemotaxis

Human neutrophils were isolated from citrated peripheral blood using standard techniques of dextran sedimentation, followed by centrifugation on Histopaque ® sterile solution (Sigma) or Ficoll-paque ® (Pharmacia) and hypotonic lysis of erythrocytes. A final cell suspension of $3.4 \times 10^6$ neutrophils/ml of HEPES-buffered Hanks' balanced salt solution (HBSS, pH 7.3) was added to the upper well (0.8 ml) of a modified Boyden chamber (blind well). The lower well (0.2 ml), separated by a polycarbonate membrane (Nuleopore Corp.), contained HBSS, $3 \times 10^{-8}$M LTB$_4$, or $1.0 \times 10^{-8}$M fMLP in the presence of absence of test compound. Following a 90 minute incubation at 37° C. in 5% CO$_2$-95% air, cells from the lower well were lysed and nuclei counted in a Model S-Plus-IV Coulter Counter. Percent inhibition was calculated from cell counts corrected for random migration by subtracting the mean of the HBSS control.

Results for representative compounds of the invention are shown in Table 1.

Data are expressed as potency relative to the compound of Example 1(b), 7-[3,(4-acetyl-3-methoxy-2-propylphenoxy) propoxy]-3,4-dihydro-8-propyl-2H-1-benzopyran-2-carboxylic acid, which is disclosed in U.S. Pat. No. 4,889,871.

TABLE 1

| | Relative Potency Values for LTB$_4$ Antagonists[1] | | |
|---|---|---|---|
| | LTB$_4$ Receptor | Chemotaxis | |
| Compound | Binding | LTB$_4$ | fMLP |
| Example 1(b) | 1.0 (0.3 µM) | 1.0 (1.8 µM) | 1.0 (5.4 µM) |
| Example 4 | 0.70 | 0.25 | 0.37 |
| Example 6 | 0.88 | 0.66 | 0.35 |

[1]Data are expressed as potency relative to a known LTB$_4$ antagonist, the compound of Example 1(b), defined as 1.0. Values in the parentheses refer to IC$_{50}$ values (µM) for the compound of Example 1(b). IC$_{50}$ is the effective concentration needed to cause 50% inhibition.

The compounds of this invention can be administered in a number of dosage forms. A preferred method of delivery would be oral or in such a manner so as to localize the action of the inhibitor. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

The compounds may be administered in a number of dosage forms, for example, such oral dosage forms as tablets, capsules, pills, powders, or granules. They may also be administered intravascularly, intraperitoneally, subcutaneously, topically or intramuscularly using forms known to the pharmaceutical art.

In general, a unit dosage of a compound of the invention would contain from about 50 mg to about 500 mg of the active ingredient with from about 70 mg to about 300 mg preferred.

An effective but non-toxic quantity of the compound is employed in treatment. The dosage regimen for inhibition of LTB$_4$ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. Generally, a dosage range of about 1 to 25 mg/kg of body weight is administered to patients in need of treatment for inflammatory conditions.

The following examples illustrate the preparation of compounds of this invention from known starting materials. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

U.S. Pat. No. 4,665,203 issued May 12, 1987, incorporated herein by reference, U.S. Pat. No. 4,889,871 issued Dec. 26, 1989, incorporated herein by reference, and European Application EP 0292977 published Nov. 30, 1988 disclose methods for making some of the intermediates used in making compounds of the present invention.

EXAMPLE 1

(a) Methyl 7-[3-(4-acetyl-3-methoxy-2-propylphenoxy) propoxy]-3,4-dihydro-8-propyl-2H-1-benzopyran-2-carboxylate for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure methyl ether, methyl 7-[3-(4-acetyl-3-methoxy-2-propylphenoxy)propoxy]-3,4-dihydro-8-propyl-2H-1-benzopyran-2-carboxylate.

EXAMPLE 1(b)

7-[3-(4-acetyl-3-methoxy-2-propylphenoxy)propoxy]-3,4-dihydro-8-propyl-2H-1-benzopyran-2-carboxylic acid

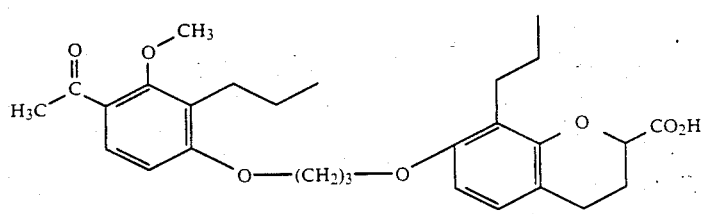

1(b)

(b) The methyl ether (1a) (340 mg) was dissolved in methanol (5 ml) containing lithium hydroxide (0.7 ml of a 2N LiOH solution in water). The mixture was stirred at room temperature overnight and the solvent removed in vacuo. The residue was partitioned between ethyl acetate and 2N HCl and the organic layer separated and washed with brine. Evaporation of the volatiles in vacuo afforded crude acid of Formula III. This material was purified by silica gel chromatography using ethyl acetate/hexane/acetic acid (40:60:0.5) as eluant. The pure product was recrystallized from ethyl acetate/hexane to afford 200 mg of product, 7-[3-(4-acetyl-3-methoxy-2-propylphenoxy)propoxy]-3,4-dihydro-8-propyl-2H-1-benzopyran-2-carboxylic acid, m.p. 65°–68° C.

Microanalysis: Found: C, 69.22; H, 7.53. Theory: C, 69.40; H, 7.49.

The NMR (CDCl$_3$) shows a —OCH$_3$ at δ3.75.

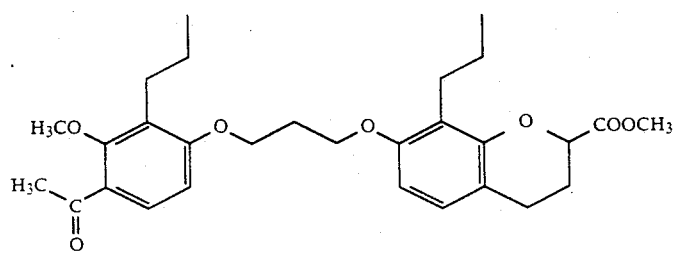

1a

Methyl 7-[3-(4-acetyl-3-hydroxy-2-propyl-phenoxy)-propoxy]-3,4-dihydro-8-propyl-2H-1-benzopyran-2-carboxylate (493 mg) was added to 25 ml of acetone containing 276 mg of anhydrous potassium carbonate and 282 mg of methyl iodide. The mixture was refluxed

EXAMPLE 2

Methyl 7-[3-[4-[3-(dimethylamino)-1-oxo-2Z-propenyl]-3-methoxy-2-propylphenoxy]propoxy]-3,4-dihydro-8-propyl-2H-1-benzopyran-2-carboxylate

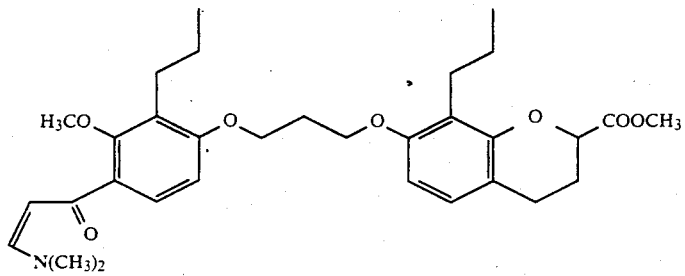

The compound of Example 1(a) (0.95 g, 1.90 mmol) was stirred in 1.0 ml of dimethylformamide (DMF) and 0.3 ml (2.26 mmol) of N,N-dimethylformamide dimethyl acetal at 110°–120° C. for 23.5 hours. The reaction mixture was cooled and poured into ethyl acetate/1.0N hydrochloric acid. The ethyl acetate layer was washed with water and brine, dried over sodium sulfate and concentrated under vacuum to give a brown gum. Flash chromatography on silica gel using 1:2 hexane/ethyl acetate followed by ethyl acetate as eluant gave the product.

Analysis calculated for $C_{32}H_{43}NO_7$. (0.3 $H_2O$): Found: C, 68.74; H, 7.80; N, 2.5 Theory: C, 68.74; H, 7.86; N, 2.51.

EXAMPLE 3

Methyl 3,4-dihydro-7-[3-[4-(3-isoxazolyl)-3-methoxy-2-propylphenoxy]propoxy]-8-propyl-2H-1-benzopyran-2-carboxylate

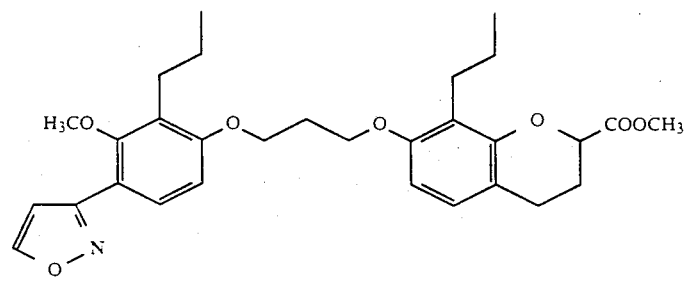

The compound of Example 2 (65 mg, 0.117 mmol) was stirred in 2.0 ml of methyl alcohol and 0.5 ml of water with 20 mg (0.29 mmol) of hydroxylamine hydrochloride, and the reaction mixture was refluxed for 1.5 hours. The reaction mixture was poured into ethyl ether and water and the ether layer was washed with brine, dried over sodium sulfate, and concentrated. Flash chromatography on silica gel using 10:1 to 5:1 hexane/ethyl acetate as eluant gave the product.

Analysis calculated for $C_{30}H_{37}NO_7$ (523.632): Found: C, 69.08; H, 7.17; N, 2.59 Theory: C, 68.81; H, 7.12; N, 2.67.

EXAMPLE 4

3,4-Dihydro-7-[3-[4-(3-isoxazolyl)-3-methoxy-2-propylphenoxy]propoxy]-8-propyl-2H-1-benzopyran-2-carboxylic acid

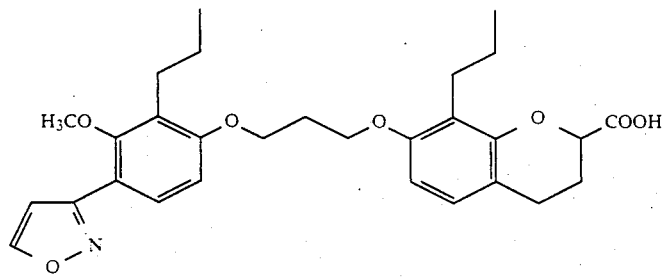

The compound of Example 3 (60 mg; 0.114 mmol), was mixed with 2.0 ml of 4:1 methanol/tetrahydrofuran (THF) and 0.18 ml of 1N lithium hydroxide. The reaction mixture was stirred at room temperature for 2.25 hours. The mixture was poured into ethyl ether and water, and the ether layer was washed with brine, dried over sodium sulfate, and concentrated. Flash chromatography of the crude product on silica gel using 5:1 to 3:1 hexane/ethyl acetate (1% acetic acid) as eluant provided the product (42 mg, 82.4 μmol, 72% yield). High resolution mass spectrum, m/e 509.2423 (calculated for $C_{29}H_{35}NO_7$, 509.2413).

EXAMPLE 5

7-[3-[4-[3-(Dimethylamino)-1-oxo-2Z-propenyl]-3-methoxy-2-propylphenoxy]propoxy]-3,4-dihydro-8-propyl-2H-1-benzopyran-2-carboxylic acid

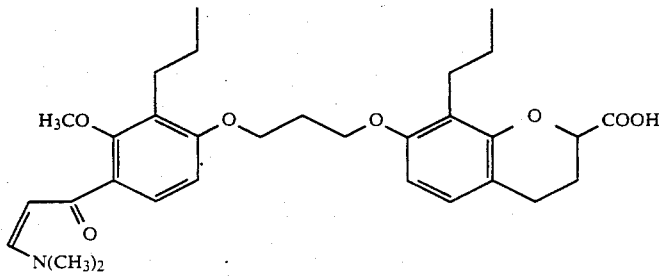

The compound of Example 2 (0.11 g, 0.199 mmol) was mixed with 3.0 ml of 4:1 methanol/THF and 0.3 ml of 1M LiOH and allowed to react at 0° C. for 15 minutes then at room temperature for 2.5 hours. The reaction mixture was poured into ethyl acetate and 0.5N hydrochloric acid, and the ethyl acetate layer was washed with brine, dried over sodium sulfate, and concentrated to give the product.

over sodium sulfate and concentrated under vacuum. Flash chromatography of the concentrate on silica gel using 5:1 to 2:1 hexane/ethyl acetate (1% acetic acid) as eluant gave the product, melting point 156°–158° C.

Analysis calculated for $C_{29}H_{36}O_6N_2 \cdot 0.3H_2O$ Found: C, 67.78; H, 7.20; N, 5.35 Theory: C, 67.76; H, 7.18; N, 5.45.

EXAMPLE 7

Methyl 7-[3-[4-[3-(dimethylamino)-1-oxo-2Z-propenyl]-3-methoxy-2-(2-propenyl)phenoxy]propoxy]-3,4-dihydro-8-propyl-2H-1-benzopyran-2-carboxylate

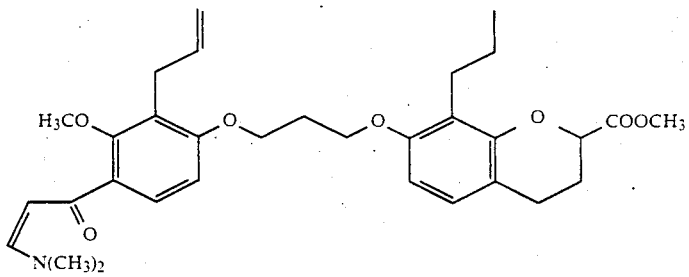

Starting with methyl 7-[3-[4-acetyl-3-methoxy-2-(2propenyl)phenoxy]-3,4-dihydro-8-propyl-2H-1-benzopyran-2-carboxylate and following the procedure described in Example 2 gives the title compound.

EXAMPLE 6

3,4-Dihydro-7-[3-[3-methoxy-2-propyl-4-(1H-pyrazol-3-yl)phenoxy]propoxy]-8-propyl-2H-1-benzopyran-2-carboxylic acid

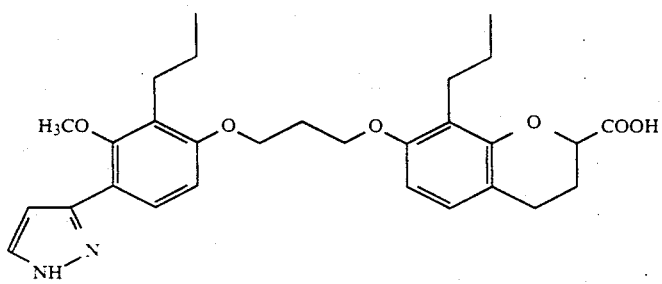

The crude compound from Example 5 was stirred in 4.0 ml of methanol/1.0 ml water with 0.1 ml hydrazine hydrate at reflux for 2.0 hours. The reaction mixture was poured into 1N hydrochloric acid/ethyl acetate, and the ethyl acetate layer was washed with brine, dried

EXAMPLE 8

Methyl 3,4-dihydro-7-[3-[3-methoxy-4-(3-isoxazolyl)-2-(2-propenyl)phenoxy]propoxy]-8-propyl-2H-1-benzopyran-2-carboxylate

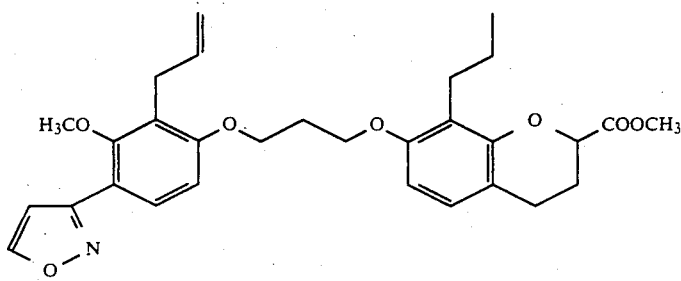

Starting with the compound of Example 7 and following the procedure described in Example 3 gives the title compound.

EXAMPLE 9

3,4-Dihydro-7-[3-[4-(3-isoxozolyl)-3-methoxy-2-(2-propenyl)phenoxy]propoxy]-8-propyl-2H-1-benzopyran-2-carboxylic acid

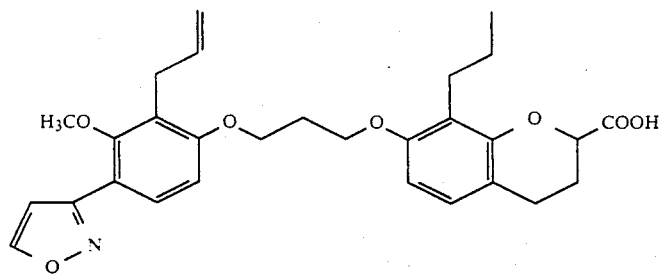

Starting with the compound of Example 8 and following the procedure described in Example 4 gives the title compound.

EXAMPLE 10

7-[3-[4-[3-(Dimethylamino)-1-oxo-2Z-propenyl]-3-methoxy-2-(2-propenyl)phenoxy]propoxy]-3,4-dihydro-8-propyl-2H-1-benzopyran-2-carboxylic acid

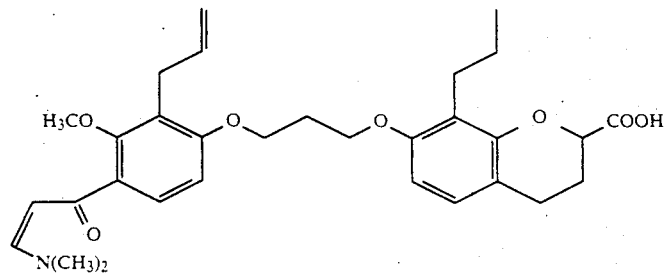

Starting with the compound of Example 7 and following the procedure described in Example 5 gives the title compound.

EXAMPLE 11

3,4-Dihydro-7-[3-[3-methoxy-2-(2-propenyl)-4-(1H-pyrazol-3-yl)phenoxy]propoxy]-8-propyl-2H-1-benzopyran-2-carboxylic acid

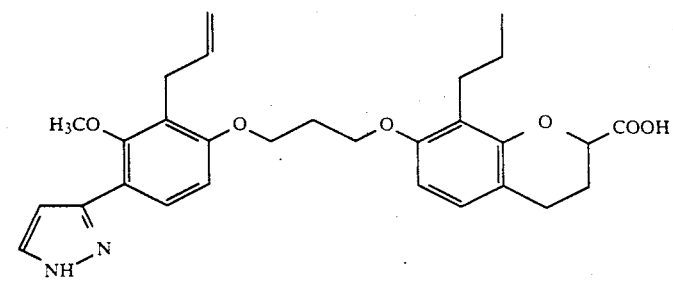

Starting with the compound of Example 10 and following the procedure described in Example 6 gives the title compound.

EXAMPLE 12

Methyl 7-[3-[2-(cyclopropylmethyl)-4-[3-(dimethylamino)-1-oxo-2Z-propenyl]-3-methoxyphenoxy]propoxy]-3,4-dihydro-8-propyl-2H-1-benzopyran-2-carboxylate

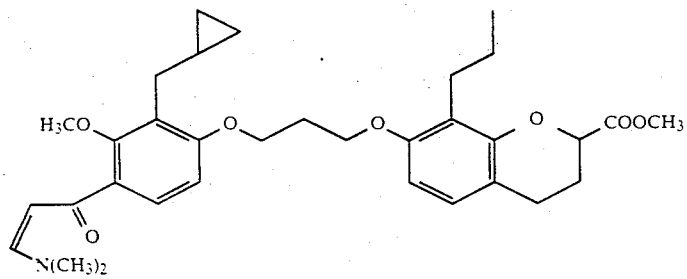

Starting with methyl 7-[3-[4-acetyl-2-(cyclopropylmethyl)-3-methoxyphenoxy]propoxy]-3,4-dihydro-8-propyl-2H-1-benzopyran-2-carboxylate and following the procedure described in Example 2 gives the title compound.

EXAMPLE 13

Methyl 3,4-dihydro-7-[3-[2-(cyclopropylmethyl)-4-(3-isoxazolyl)-3-methoxyphenoxy]propoxy]-8-propyl-2H-1-benzopyran-2-carboxylate

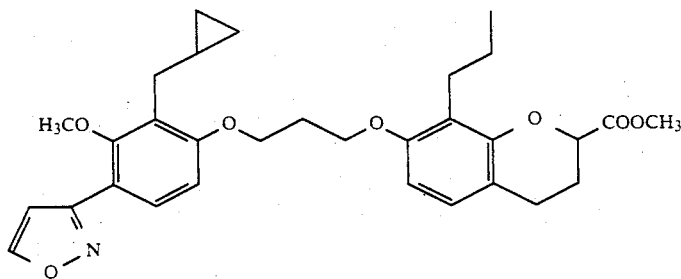

Starting with the compound of Example 12 and following the procedure described in Example 3 gives the title compound.

EXAMPLE 14

3,4-Dihydro-7-[3-[2-(cyclopropylmethyl)-4-(3-isoxazolyl)-3-methoxyphenoxy]propoxy]-8-propyl-2H-1-benzopyran-2-carboxylic acid

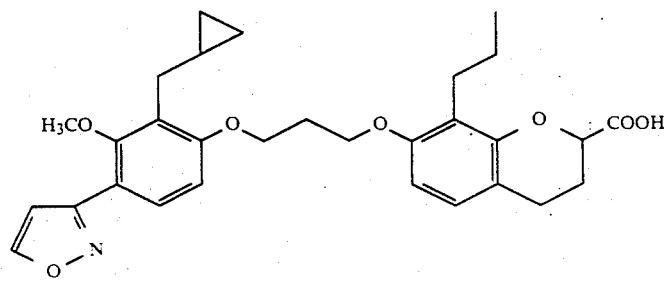

Starting with the compound of Example 13 and following the procedure described in Example 4 gives the title compound.

EXAMPLE 15

7-[3-[2-(Cyclopropylmethyl)-4-[3-(dimethylamino)-1-oxo-2Z-propenyl]-3-methoxyphenoxy]propoxy]-3,4-dihydro-8-propyl-2H-1-benzopyran-2-carboxylic acid

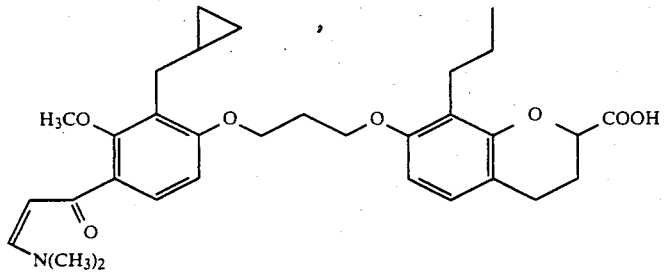

Starting with the compound of Example 12 and following the procedure described in Example 5 gives the title compound.

EXAMPLE 16

3,4-Dihydro-7-[3-[2-(cyclopropylmethyl)-3-methoxy-4-(1H-pyrazol-3-yl)phenoxy]propoxy]-8-propyl-2H-1-benzopyran-2-carboxylic acid

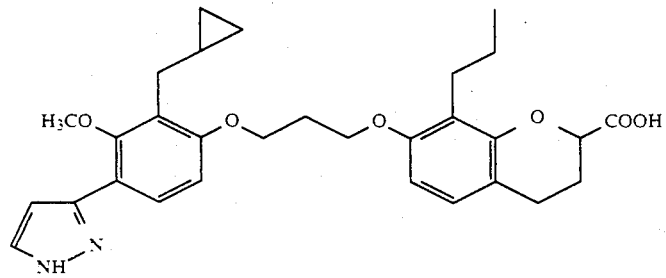

Starting with the compound of Example 15 and following the procedure described in Example 6 gives the title compound.

What is claimed is:

1. A compound of the formula:

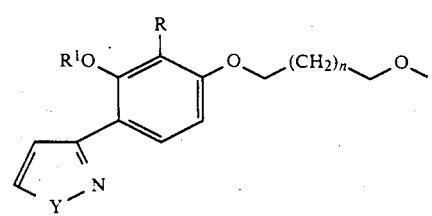

-continued

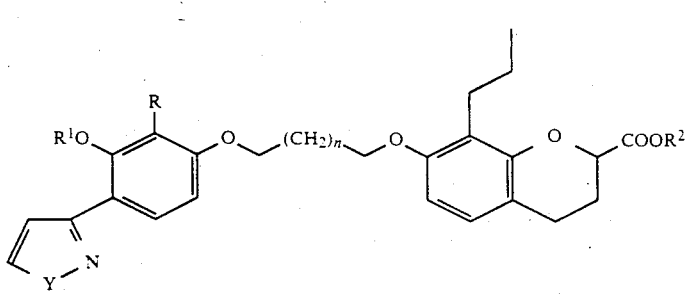

wherein
R represents alkyl having 2 to 6 carbon atoms, alkenyl having 2 to 6 carbon atoms, alkynyl having 2 to 6 carbon atoms, or $—(CH_2)_m—R^3$ wherein $R^3$ represents cycloalkyl of 3 to 5 carbons atoms and m is 1 or 2;
$R^1$ represents alkyl having 1 to 4 carbon atoms;
$R^2$ represents hydrogen or alkyl having 1 to 5 carbon atoms;
$R^4$ represents alkyl having 1 to 6 carbon atoms;
n is an integer from 1 to 5; and
Y represents NH or oxygen; and the stereoisomers and pharmaceutically acceptable salts thereof.

2. A compound according to claim 1 of the formula wherein
R represents alkyl having 2 to 4 carbon atoms alkenyl having 3 to 4 carbon atoms, or cyclopropylalkyl wherein the alkyl moiety has 1 to 2 carbon atoms;
$R^1$ represents methyl or ethyl;
$R^2$ represents hydrogen or alkyl having 1 to 3 carbon atoms;

n is an integer from 1 to 3; and

Y represents NH or oxygen; and the stereoisomers and pharmaceutically acceptable salts thereof.

3. A compound according to claim 1 of the formula

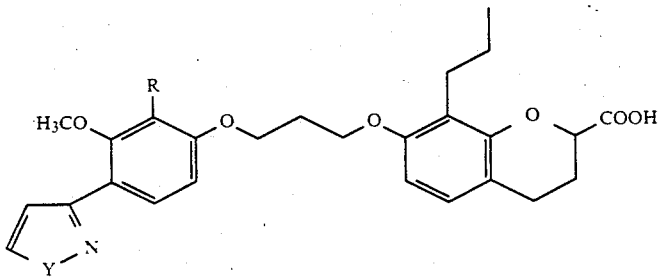

wherein
R represents propyl, 2-propenyl, or cyclopropylmethyl; and
Y represents NH or oxygen; and the stereoisomers and pharmaceutically acceptable salts thereof.

4. A compound according to claim 3 which is 3,4-dihydro-7-[3-[4-(3-isoxazolyl)-3-methoxy-2-propylphenoxy]propoxy]-8-propyl-2H-1-benzopyran-2-carboxylic acid.

5. A compound according to claim 3 which is 3,4-dihydro-7-[3-[3-methoxy-2-propyl-4-(1H-pyrazol-3-yl)phenoxy]propoxy]-8-propyl-2H-1-benzopyran-2-carboxylic acid.

6. A pharmaceutical composition for treating leukotriene $B_4$ mediated diseases comprising a therapeutically effective amount of a compound of claim 1 and a pharmaceutically acceptable carrier.

7. A pharmaceutical composition for treating inflammatory diseases comprising a therapeutically effective amount of a compound of claim 1 and a pharmaceutically acceptable carrier.

8. A pharmaceutical composition for treating inflammatory diseases comprising a therapeutically effective amount of a compound of claim 2 and a pharmaceutically acceptable carrier.

9. A pharmaceutical composition for treating inflammatory diseases comprising a therapeutically effective amount of a compound of claim 3 and a pharmaceutically acceptable carrier.

10. A pharmaceutical composition for treating inflammatory diseases comprising a therapeutically effective amount of a compound of claim 4 and a pharmaceutically acceptable carrier.

11. A pharmaceutical composition for treating inflammatory diseases comprising a therapeutically effective amount of a compound of claim 5 and a pharmaceutically acceptable carrier.

12. A method of treating leukotriene $B_4$ mediated diseases comprising administering to a mammal in need of such treatment a therapeutically effective amount of a compound of claim 1.

13. A method of treating inflammatory diseases comprising administering to a mammal in need of such treatment a therapeutically effective amount of a compound of claim 1.

14. A method of treating inflammatory diseases comprising administering to a mammal in need of such treatment a therapeutically effective amount of a compound of claim 2.

15. A method of treating inflammatory diseases comprising administering to a mammal in need of such treatment a therapeutically effective amount of a compound of claim 3.

16. A method of treating inflammatory diseases comprising administering to a mammal in need of such treatment a therapeutically effective amount of a compound of claim 4.

17. A method of treating inflammatory diseases comprising administering to a mammal in need of such treatment a therapeutically effective amount of a compound of claim 5.

18. A method according to claim 13 wherein the inflammatory disease is rheumatoid arthritis.

19. A method according to claim 13 wherein the inflammatory disease is psoriasis.

20. A method according to claim 13 wherein the inflammatory disease is inflammatory bowel disease.

21. A method according to claim 13 wherein the inflammatory disease is gout.

22. A method according to claim 14 wherein the inflammatory disease is asthma.

23. A method according to claim 13 wherein the inflammatory disease is multiple sclerosis.

* * * * *

UNITED STATES PATENT AND TRADEMARK OFFICE
CERTIFICATE OF CORRECTION

PATENT NO. : 5,051,438

DATED : September 24, 1991

INVENTOR(S) : Djuric, et al.

It is certified that error appears in the above-identified patent and that said Letters Patent is hereby corrected as shown below:

Column 9, line 44, reading "2.5Theory:" should read -- 2.51. Theory --.

Column 12, line 45 reading "(2propenyl)" should read -- (2-propenyl) --

Signed and Sealed this

Seventeenth Day of August, 1993

*Attest:*

BRUCE LEHMAN

*Attesting Officer*     *Commissioner of Patents and Trademarks*